United States Patent [19]
Gedridge, Jr.; Robert W. et al.

[11] Patent Number: 5,456,207
[45] Date of Patent: Oct. 10, 1995

[54] SYNTHESIS OF TRIISOPROPYLINDIUM DIISOPROPYLTELLURIDE ADDUCT AND USE FOR SEMICONDUCTOR MATERIALS

[75] Inventors: Robert W. Gedridge, Jr., Ridgecrest, Calif.; Ralph Korenstein, Framingham, Mass.; Stuart JC. Irvine, Hope, United Kingdom

[73] Assignee: The United States of America as represented by the Secretary of the Navy, Washington, D.C.

[21] Appl. No.: 245,311

[22] Filed: May 16, 1994

[51] Int. Cl.$^6$ .................................................. C30B 25/02
[52] U.S. Cl. .................... 117/104; 117/953; 117/954; 117/956; 117/957
[58] Field of Search .................... 117/104, 953, 117/954, 956, 957; 437/104

[56] References Cited

U.S. PATENT DOCUMENTS

| | | | |
|---|---|---|---|
| 4,636,268 | 11/1987 | Tsang | 117/104 |
| 4,734,387 | 3/1988 | Nelson et al. | 117/104 |
| 4,804,638 | 2/1989 | Hoke et al. | 437/81 |
| 5,324,386 | 6/1994 | Murakami et al. | 117/98 |

FOREIGN PATENT DOCUMENTS

| | | | |
|---|---|---|---|
| 03023299 | 1/1991 | Japan | 117/104 |

OTHER PUBLICATIONS

Journal of Electronic Materials, vol. 22, No. 8 Korenstein et al. published Jun., 1993, "Indium Doping of HgCdTe Grown by Metalorganic Chemical Vapor Deposition–Direct Alloy Growth Using Triisopropylindium and Diisopropyltellurium Triisopropylindium Adduct".

Journal of Electronic Materials, vol. 22, No. 8 Irvine et al. published Jun., 1993, "A New N–Type Doping Precursor for MOCVD–IMP Growth of Detector Quality MCT".

Maier et al., "Growth, Properties and Applications of Narrow–Gap Semiconductors" in Crystals vol. 4, Springer–Verlag, New York 1980 pp. 176–177.

Ploog, "Molecular Beam Epitaxy of III–V Compounds" in Crystals, vol. 3 Springer–Verlag, New York, 1980 p. 115.

Robert W. Gedridge, Jr. et al., 08027314 filed Feb. 25, 1993.

*Primary Examiner*—Robert Kunemund
*Attorney, Agent, or Firm*—Melvin J. Sliwka; John L. Forrest, Jr.

[57] ABSTRACT

Triisopropylindium diisopropyltelluride adduct, $((CH_3)_2CH)_3In:Te(CH(CH_3)_2)_2$ is synthesized and is used as a universal n-type dopant for both II/VI semiconductor materials as well as III/V semiconductor materials is disclosed. This dopant precursor is particularly suited for indium doping of II/V semiconductor materials at low carrier concentrations down to $10^{14}$ cm$^{-3}$ and does not exhibit an appreciable memory effect.

23 Claims, No Drawings

SYNTHESIS OF TRIISOPROPYLINDIUM DIISOPROPYLTELLURIDE ADDUCT AND USE FOR SEMICONDUCTOR MATERIALS

BACKGROUND OF THE INVENTION

1. Field of the Invention

The present invention relates in general to the doping of semiconductor materials, and more particularly, to the use of triisopropylindium diisopropyltelluride adduct as a dopant precursor in the chemical vapor deposition of II/VI and III/V semiconductor materials.

2. Related Art

The II/VI semiconductor materials such as mercury cadmium telluride (HgCdTe) and cadmium telluride (CdTe) and III/V semiconductor materials such as indium antimony (InSb) have many applications both in the military as well as the commercial sector. A particularly important application of the II/VI and III/V semiconductor materials is in infrared detectors. There exist a variety of binary semiconductor systems such as HgTe, CdTe, ZnSe, and InSb as well as many ternary and quaternary semiconductor systems such as HgCdTe, InAsSb, and GaInAsSb that have been investigated for applications in infrared emitters and detectors operating in the 3–5 µm and 8–12 µm spectral ranges. These wavelength ranges are particularly important because they are natural windows in the atmosphere for infrared transmission. In addition, many II/VI semiconductor materials are also potential candidates for efficient solar cells and other advanced optoelectronic devices.

Many of these advanced applications require controlled extrinsic doping of both p-type and n-type semiconductor materials. Various related art has demonstrated metalorganic chemical vapor deposition (MOCVD) of p-type HgCdTe doped with arsenic using both arsine and tertiarybutylarsine. However, low level doping of n-type HgCdTe, in the range of $10^{14}$ atoms per $cm^3$ to $10^{15}$ atoms per $cm^3$, remains more of a problem.

A variety of approaches have been used to control the doping of n-type HgCdTe grown by metal-organic chemical vapor deposition (MOCVD). These include group III doping onto the group II site using Al, Ga and In and group VII doping onto the group VI site using iodine. A common problem with the precursors developed for III-V MOCVD is that their saturated vapor pressures are too high to be handled conveniently as dopant precursors. Lower dopant concentrations can be obtained from an effuser source but there is less flexibility in the range of concentrations from vapor pressure simply controlled by the source temperature. A potentially more serious problem is unwanted reaction processes that cause a memory effect where doping will persist for a number of growth runs following its introduction.

Indium is the dopant of choice for producing n-type HgCdTe due to its slow diffusion in HgCdTe compared to other n-type dopants. It has been used to produce n-type HgCdTe grown by MOCVD using both an interdiffused multilayer process and directed alloy growth. Most of the work to date has utilized trimethylindium as the indium dopant precursor.

However, as disclosed in U.S. patent application Ser. No. 08/027,314, there are several problems generally associated with the use of trimethylindium. Since trimethylindium is a solid at or below room temperature, the effective vapor pressure of trimethylindium in a conventional bubbler changes with time due to changes in the surface area of solid. This often results in transport problems. Furthermore, the use of trimethylindium in low temperature processes can result in unintentional carbon impurity incorporation, due to the formation of methyl radicals during pyrolysis, which can be deleterious to the ultimate performance of a semiconductor device.

To that end, trimethylindium is not a suitable precursor for doping HgCdTe at low concentrations. Because of its relatively high vapor pressure the lowest doping achieved to date with trimethylindium is in the mid $10^{16}$ $cm^{-3}$. In addition, trimethylindium has shown a significant 'memory' effect, where indium has been detected in un-doped growths.

Even though trimethylindium has been used successfully as a source compound for indium containing semiconductor materials, trimethylindium has several noted problems when used as a low level n-type dopant in HgCdTe. Thus a given compound which may demonstrate acceptable results when used as a source compound for semiconductor materials does not mean that the same compound can be used as dopant source for semiconductor materials with equally good results.

What is desired is preferably a liquid dopant precursor which can provide a constant quantity of indium or telluride dopant and has a very low vapor pressure at reasonable temperatures to allow n-type doping at low carrier concentrations. The memory effect of the dopant precursor should preferably be minimal or non-existent.

SUMMARY OF THE INVENTION

Triisopropylindium diisopropyltelluride adduct, $((CH_3)_2CH)_3In:Te(CH(CH_3)_2)_2$ can be prepared and isolated by reacting purified triisopropylindium with purified diisopropyl telluride. This general reaction produces compounds having the general formula $(R)_3In:Te(R)_2$, where R=organo groups. These compounds can be used as n-type dopants in II/VI semiconductor materials as well as III/V semiconductor materials. Using these compounds to deposit indium will result in n-type II/VI semiconductor materials if indium is electrically active and desirable for a specific II/VI semiconductor system. If the compounds are used to deposit telluride, n-type III/V semiconductor materials will result if tellurium is electrically active and desirable for a specific III/V semiconductor system.

Accordingly, it is an object of the present invention to provide triisopropylindium diisopropyltelluride adduct for use as a universal n-type dopant for both II/VI semiconductor materials and III/V semiconductor materials.

Yet another object of the present invention is to provide an indium precursor for doping II/VI semiconductor materials such as HgCdTe at concentrations in the range of the low $10^{15}$ $cm^{-3}$ or less.

Yet another object of the present invention is to provide a tellurium precursor for doping III/V semiconductor materials.

Still another object of the present invention is to provide an improved process for doping II/VI semiconductor materials using a metalorganic chemical vapor deposition (MOCVD) process. In this improved process, triisopropylindium diisopropyltelluride adduct, $((CH_3)_2CH)_3In:Te(CH(CH_3)_2)_2$, is used as a source of indium to dope II/VI semiconductor materials or as a source of tellurium to dope III/V semiconductor materials.

An important object of the invention is to provide an indium or tellurium semiconductor precursor that is a liquid which has a much lower vapor pressure than most trialkylindium compounds and is not pyrophoric like most trialkylindium compounds.

A further object of the present invention is to provide an indium or tellurium semiconductor precursor that is not photosensitive under normal room light conditions.

These and other objects, features and advantages will become apparent from a thorough consideration of the detailed description which follows.

DETAILED DESCPTION OF THE INVENTION

From the foregoing, it is seen that the disclosed invention provides an improved process for doping II/VI and III/V semiconductor materials using a metalorganic chemical vapor deposition (MOCVD) process. The preferred dopants are either indium or tellurium. The preferred chemical vapor deposition process for producing indium or tellurium doped semiconductor materials is the process known as MOCVD. However, other chemical vapor deposition process such as APCVD, LPCVD, CBE and MOMBE can also be utilized.

MOCVD is high throughput technique for the production of high quality III/V and II/VI semiconductor materials and complex structures such as superlattices and focal plane arrays using organometallic precursors.

Indium containing semiconductor materials have been grown by MOCVD using conventional organo-indium dopant precursors such as trimethylindium, triethylindium, ethyldimethylindium and cyclopentadiethylindium. The most common MOCVD indium dopant precursor presently employed is trimethylindium. As discussed above, trimethylindium has several disadvantages including a significant memory effect, a variable effective vapor pressure, and an inability to achieve low concentrations of indium doping.

Triisopropylindium diisopropyltelluride adduct is a compound containing purified triisopropylindium and purified diisopropyltelluride. This Lewis Base Lewis Acid complex is a true compound with a unique spectroscopic signature. It is anticipated that similar compounds may also be used in lieu of triisopropylindium diisopropyltelluride adduct. Specifically, these compounds would have the general formula:

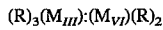

$(R)_3(M_{III}):(M_{VI})(R)_2$ where R is an organo group, preferably an alkyl group, $M_{III}$ is a Group IIIA metal, and $M_{VI}$ is a Group VIA metal or element. The preferred Group IIIA metal is indium, however, the Group IIIA metals aluminum and gallium may also be effective. Likewise, the preferred Group VI element is tellurium, however, the use of selenium would also be possible.

The triisopropylindium diisopropyltelluride adduct has a melting point of less than $-78°$ C., and thus is a significantly better indium dopant source than trimethylindium. Since triisopropylindium diisopropyltelluride adduct is a liquid at these very low temperatures, it offers better control of the indium doping process, indium doping at lower temperatures, indium doping at lower concentrations, and a drastic reduction of the memory effect. The triisopropylindium diisopropyltelluride adduct also can act as a tellurium precursor for doping III/V semiconductor materials. Thus, triisopropylindium diisopropyltelluride adduct can be used as a universal dopant for both II/VI and III/V semiconductor materials.

A particlar advancement offerred by the use of triisopropylindium diisopropyltelluride adduct as an indium n-type doping source for the n-type doping of HgCdTe at low levels $(3.7 \times 10^{14}$ cm$^{-3})$ has not been possible using the conventional doping source trimethylindium. Indium n-type doping of HgCdTe at low levels $(1.5 \times 10^{14}$ cm$^{-3})$ has been possible using the doping source triisopropylindium as disclosed in U.S. patent application Ser. No. 08/027,314. Doping levels of approximately $10^{17}$ cm$^{-3}$ to $10^{18}$ cm$^{-3}$ are typical with current commercially available reagents. However background doping of about mid $10^{16}$ cm$^{-3}$ is typical due to the memory effect using commercially available reagents such as trimethylindium. The new dopant precursor triisopropylindium diisopropyltelluride adduct allows doping as low as $3.7 \times 10^{14}$ cm$^{-3}$ and does not exhibit a substantial memory effect.

EXAMPLES

Example I: Synthesis of Triisopropylindium Diisopropyltelluride Adduct

A preferred method of preparing, isolating and purifying triisopropylindium diisopropyltelluride adduct is set forth in the following paragraphs.

Triisopropylindium, $((CH_3)_2CH)_3In$, was synthesized be reaction of anhydrous indium chloride with 3.5 equivalents of isopropylmagnesium chloride in diethyl ether. The diethyl ether was removed under vacuum at room temperature and the residue was extracted with hexane. After filtration, the solvents were removed by fractional vacuum distillation and the crude product was collected in a $N_2$ trap. The light-yellow liquid was then heated to 75° C. and refluxed at 3 torr using a $-13°$ C. condenser for 4 hours in the dark to remove any traces of solvent. The product was then purified by fractional vacuum distillation two more times. The first purification process was performed at 60° C. and 2.0 Torr while the second purification process occurred at 53° C. and 1.2 Torr. The result was a light-sensitive light-yellow pyrophoric liquid in approximately 50–55% yield. The desired compound was confirmed by $^1H$ and $^{13}C$ NMR spectroscopy. Diisopropyltelluride, $((CH_3)_2CH)_2Te$, is preferably made by conventional methods and also purified by fractional vacuum distillation.

To the purified triisopropylindium, is added at room temperature greater than one equivalent of purified diisopropyltelluride. The pale yellow liquid is stirred at room temperature for greater than 3 hours under a dynamic vacuum of approximately $10^{-3}$ Torr in order to remove the excess diisopropyltelluride. The result is a quantitative yield of triisopropylindium adduct, $((CH_3)_2CH)_3In:Te(CH(CH_3)_2)_2$, a pale non-pyrophoric yellow liquid with a melting point less than $-78°$ C. The desired compound was confirmed by $^1H$ and $^{13}C$ NMR spectroscopy. The following Table summarizes the NMR spectroscopy results.

TABLE I $^1H$ and $^{13}C$ NMR Spectroscopy of Triisopropylindium Diisopropyltelluride Adduct

| $^1H$ NMR Spectroscopy: | |
|---|---|
| septet, Te—CH | 3.11 ppm |
| doublet of doublet, $CH_3$ on triisopropylindium | 1.63 ppm |
| doublet, $CH_3$ on diisopropyltelluride | 1.37 ppm |
| multiplet, CH—In | 1.32 ppm |
| $^{13}C$ NMR Spectroscopy: | |
| quartet of multiplets, $CH_3$ on diisopropyltelluride | 26.71 ppm |

TABLE I-continued

$^1$H and $^{13}$C NMR Spectroscopy of Triisopropylindium Diisopropyltelluride Adduct

| | |
|---|---|
| quartet of multiplets, CH$_3$ on triisopropylindium | 24.93 ppm |
| doublet, CH on triisopropylindium | 22.20 ppm |
| doublet, CH on diisopropyltelluride | 14.41 ppm |

The adduct does not lose diisopropyltelluride at room temperature under vacuum, but heating the triisopropylindium diisopropyltelluride adduct to approximately 65°–70° C. under vacuum results in the loss of diisopropyltelluride.

In contrast to trialkylindium compounds, triisopropylindium diisopropyltelluride adduct is not pyrophoric. It is a liquid with a much lower vapor pressure than trimethylindium or triisopropylindium. It also has a melting point less than −78° C. It does not appear to be photosensitive under normal room light conditions. All these properties make triisopropylindium diisopropyltelluride adduct an ideal dopant for both n-type II/VI and III/V semiconductor materials.

The adduct indium precursor triisopropylindium diisopropyltelluride has a significantly lower vapor pressure than either trimethylindium or triisopropylindium. In fact, the vapor pressure of trimethylindium is approximately ten times higher at room temperature than that of triisopropylindium but is comparable at approximately −15° C. One particular advantage of using triisopropylindium diisopropyltelluride adduct at low temperatures is that it is a liquid compared to solid trimethylindium. On the other hand, the vapor pressure of triisopropylindium diisopropyltelluride adduct is about 100 times lower than trimethylindium at −15° C. and it is still a liquid.

Example II: Use of Triisopropylindium Diisopropyltelluride Adduct as Indium Dopant HgCdTe was grown on CdTe substrates by the MOVCD direct alloy growth process in a horizontal reactor at approximately 360° C. using diisopropyltelluride, dimethylcadmium and elemental mercury. The triisopropylindium diisopropyltelluride adduct, was used as an indium dopant precursor and was contained in a standard cylinder and operated in the conventional bubbler mode. The composition of the grown layers was determined from infrared transmission and thickness measurements. Samples were annealed at 220° C. for 15 hours in a Hg ambient environment to eliminate Hg vacancies. Carrier concentration and mobility were determined from Van der Pauw measurements performed at room temperature and 77K.

Because of the lower vapor pressure of the triisopropylindium diisopropyltelluride adduct, the bubbler can be kept at or near room temperature thus simplifying its use. In addition, the lower vapor pressure allows the process to incorporate larger flow rates of the hydogen or other carrier gas through the bubbler. This large flow rates of the carrier gas allows for greater control of the deposition process and is important in order to achieve the low carrier concentrations.

Triisopropylindium diisopropyltelluride adduct was introduced into the reactor in the same stainless steel manifold as the dimethylcadmium compound and the bubbler was maintained at 22° C. The triisopropylindium diisopropyltelluride adduct could also be introduced into the reactor via the same stainless steel manifold as the diisopropyltelluride compound. As mentioned above, the HgCdTe were grown onto CdTe substrates and misoriented 4°. In addition, a CdTe buffer layer was first grown on the substrate by MOCVD prior to HgCdTe deposition. Table II lists some of the material characteristics of HgCdTe doped with the adduct compound. The epilayers are n-type and could be doped from the mid $10^{14}$ cm$^{-3}$ range to the low $10^{18}$ cm$^{-3}$ range. There appears to be good agreement between the carrier concentrations ($n_H$) determined from Hall measurements and indium concentration determined from the secondary ion mass spectrscopy (SIMS) results indicating near 100% indium activation in these layers.

TABLE II

Characteristics of Indium Doped HgCdTe Semiconducting Material Using Triisopropylindium Diisopropyltelluride Adduct

| Sample | x | $n_H$ 77K (cm$^{-3}$) | $\mu^{77K}$ (cm$^{-3}$) | SIMS Indium (cm$^{-3}$) (surface) | SIMS Indium (cm$^{-3}$) (Interface) |
|---|---|---|---|---|---|
| 1697 | 0.271 | $3.7 \times 10^{14}$ | $7.3 \times 10^4$ | $4.0 \times 10^{14}$ | $4.0 \times 10^{14}$ |
| 1685 | 0.243 | $3.0 \times 10^{15}$ | $7.3 \times 10^4$ | $4.0 \times 10^{15}$ | $4.0 \times 10^{15}$ |
| 1683 | 0.235 | $2.7 \times 10^{16}$ | $7.1 \times 10^4$ | ** | ** |
| 1680 | 0.295 | $2.0 \times 10^{18}$ | $1.0 \times 10^4$ | $4.0 \times 10^{18}$ | $1.0 \times 10^{17}$ |

Example III: Use of Triisopropylindium Diisopropyltelluride Adduct as Tellurium Dopant The following is a descriptive example of the use of triisopropylindium diisopropyltelluride adduct as a source of tellurium to prepare n-type III/V semiconductor materials. For example, epitaxial Indium-Antimonide (InSb) can be grown by MOCVD using trimethylindium as the indium source, and trimethylantimony as the antimony source. Using the triisopropylindium diisopropyltelluride adduct, as described in Example II above, will result in tellurium doped n-type InSb semiconductor material. For purposes of this example, the triisopropylindium diisopropyltelluride adduct should be introduced into the reactor using a separate stainless steel manifold as the trimethylantimony compound and the bubbler should be maintained at 22° C.

From the foregoing description, those persons skilled in the art can easily ascertain the essential characteristics of this invention, and without departing from the spirit and scope thereof, can make various changes and modifications in the synthesis and use of Triisopropylindium Diisopropyltelluride Adduct. Therefore, it is not intended that the scope of this invention be limited to the specific examples described. Rather it is intended that the scope of the invention be determined by appending claims and their equivalents.

What we claim the invention is:

1. An adduct for use in semiconductor materials having the general formula: $(R)_3(M_{III}){:}(M_{VI})(R)_2$, where R is an organo group, $M_{III}$ is a Group IIIA element, and $M_{VI}$ is a Group VIA element.

2. The adduct of claim 1 wherein the Group IIIA elements are selected from the group consisting of boron, aluminum, gallium, and indium.

3. The adducts of claim 1 wherein the Group VI metals are selected from the group consisting of sulfur, selenium, and tellurium.

4. An adduct for use in semiconductor materials having the general formula: $(R')_3In{:}Te(R'')_2$, where R' and R'' are organo groups.

5. The adduct of claim 1 having the formula $((CH_3)_2CH)_3In:Te(CH(CH_3)_2)_2$.

6. A process for indium doping a Group II/Group VI semiconductor material by chemical vapor deposition wherein the indium source is triisopropylindium diisopropyltelluride adduct.

7. The process of claim 6, wherein said one or more sources of said Group II material is a compound containing an element selected from the group consisting of cadmium, mercury, and zinc.

8. The process of claim 6, wherein said one or more sources of said Group VI material is a compound containing an element selected from the group consisting of sulfur, selenium, and tellurium.

9. The process of claim 6, wherein said Group II/Group VI semiconductor material is selected from the group consisting of binary, ternary and quaternary Group II/Group VI semiconductor materials.

10. The process of claim 6, wherein the indium doping concentration of said doping reaction taking place at a carrier concentration ranging from about $10^{19}$ cm$^{-3}$ to about $10^{14}$ cm$^3$.

11. A process for indium doping a Group II/Group VI semiconductor material by chemical vapor deposition which comprises reacting triisopropylindium diisopropyltelluride adduct and one or more sources of a Group II material and one or more sources of a Group VI material by chemical vapor deposition at a temperature sufficiently high to at least partially decompose the triisopropylindium diisopropyltelluride adduct and said Group II and said Group VI source materials, and depositing the materials on a semiconductor substrate.

12. The process of claim 11, wherein said one or more sources of said Group II material is a compound containing an element selected from the group consisting of cadmium, mercury, and zinc.

13. The process of claim 11, wherein said one or more sources of said Group VI material is a compound containing an element selected from the group consisting of sulfur, selenium, and tellurium.

14. The process of claim 11, wherein said Group II/Group VI semiconductor material is selected from the group consisting of binary, ternary and quaternary Group II/Group VI semiconductor materials.

15. The process of claim 11, wherein the indium doping concentration of said doping reaction taking place at a carrier concentration ranging from about $10^{19}$ cm$^{-3}$ to about $10^{14}$ cm$^3$.

16. A process for tellurium doping a Group III/Group V semiconductor material by chemical vapor deposition wherein the tellurium source is triisopropylindium diisopropyltelluride adduct.

17. The process of claim 16, wherein said one or more sources of said Group III material is a compound containing an element selected from the group consisting of boron, indium, gallium, and aluminum.

18. The process of claim 16, wherein said one or more sources of said Group V material is a compound containing an element selected from the group consisting of antimony, arsenic, phosphorous, and bismuth.

19. The process of claim 16, wherein said Group III/Group V semiconductor material is selected from the group consisting of binary, ternary and quaternary Group III/Group V semiconductor materials.

20. A process for tellurium doping a Group III/Group V semiconductor material by chemical vapor deposition which comprises reacting triisopropylindium diisopropyltelluride adduct and one or more sources of a Group III material and one or more sources of a Group V material by chemical vapor deposition at a temperature sufficiently high to at least partially decompose the triisopropylindium diisopropyltelluride adduct and said Group III and said Group V source materials, and depositing the materials on a semiconductor substrate such that minimal memory doping occurs.

21. The process of claim 20, wherein said one or more sources of said Group II material is a compound containing an element selected from the group consisting of boron, indium, gallium, and aluminum.

22. The process of claim 20, wherein said one or more sources of said Group VI material is a compound containing an element selected from the group consisting of antimony, arsenic, phosphorous, and bismuth.

23. The process of claim 20, wherein said Group III/Group V semiconductor material is selected from the group consisting of binary, ternary and quaternary Group III/Group V semiconductor materials.

* * * * *